United States Patent
Zen

(10) Patent No.: US 9,967,442 B2
(45) Date of Patent: May 8, 2018

(54) ENDOSCOPE APPARATUS

(71) Applicant: OLYMPUS CORPORATION, Tokyo (JP)

(72) Inventor: Kenichi Zen, Tachikawa (JP)

(73) Assignee: OLYMPUS CORPORATION, Tokyo (JP)

(*) Notice: Subject to any disclaimer, the term of this patent is extended or adjusted under 35 U.S.C. 154(b) by 368 days.

(21) Appl. No.: 14/987,102

(22) Filed: Jan. 4, 2016

(65) Prior Publication Data

US 2016/0119521 A1 Apr. 28, 2016

Related U.S. Application Data

(63) Continuation of application No. PCT/JP2014/063105, filed on May 16, 2014.

(30) Foreign Application Priority Data

Jul. 4, 2013 (JP) .................. 2013-140808

(51) Int. Cl.
*H04N 5/225* (2006.01)
*G02B 23/24* (2006.01)
(Continued)

(52) U.S. Cl.
CPC ....... *H04N 5/2254* (2013.01); *A61B 1/00032* (2013.01); *A61B 1/00096* (2013.01);
(Continued)

(58) Field of Classification Search
None
See application file for complete search history.

(56) References Cited

U.S. PATENT DOCUMENTS

2010/0208046 A1 8/2010 Takahashi
2011/0319712 A1* 12/2011 Kuroda .................. A61B 1/05
600/109

(Continued)

FOREIGN PATENT DOCUMENTS

JP H07-163517 6/1995
JP H10-082957 3/1998
(Continued)

OTHER PUBLICATIONS

Extended Supplementary European Search Report dated Mar. 2, 2017 in European Patent Application No. 14 82 0690.7.
(Continued)

*Primary Examiner* — Andy Rao
*Assistant Examiner* — Samuel D Fereja
(74) *Attorney, Agent, or Firm* — Scully, Scott, Murphy & Presser, P.C.

(57) ABSTRACT

An endoscope apparatus includes a first optical system, a second optical system, a light-blocking shutter, a magnet rotor, drive coils, detection coils, and a CPU, the CPU performs control to provide direct current to the drive coils and control to provide alternating current to the detection coils, and where the alternating current is provided to the detection coils, the CPU detects a pivotal position of the light-blocking shutter by detecting variation of an inductance when a magnetic field generated in each of hollow portions of the detection coils is blocked by a magnetic body, from a value of the alternating current.

14 Claims, 12 Drawing Sheets

(51) Int. Cl.
*G02B 26/02* (2006.01)
*A61B 1/00* (2006.01)
*A61B 1/045* (2006.01)

(52) U.S. Cl.
CPC ...... *A61B 1/00133* (2013.01); *A61B 1/00188* (2013.01); *A61B 1/045* (2013.01); *G02B 23/243* (2013.01); *G02B 26/023* (2013.01)

(56) References Cited

U.S. PATENT DOCUMENTS

| | | | | |
|---|---|---|---|---|
| 2012/0136213 | A1* | 5/2012 | Weimer | A61B 1/00066 600/173 |
| 2014/0210945 | A1* | 7/2014 | Morizumi | A61B 1/00096 348/45 |

FOREIGN PATENT DOCUMENTS

| | | |
|---|---|---|
| JP | 2010-128354 A | 6/2010 |
| JP | 4750175 B2 | 8/2011 |
| JP | 2013-253797 A | 12/2013 |

OTHER PUBLICATIONS

International Search Report dated Aug. 26, 2014 issued in PCT/JP2014/063105.

* cited by examiner

ENDOSCOPE APPARATUS

CROSS REFERENCE TO RELATED APPLICATION

This application is a continuation application of PCT/JP2014/063105 filed on May 16, 2014 and claims benefit of Japanese Application No. 2013-140808 filed in Japan on Jul. 4, 2013, the entire contents of which are incorporated herein by this reference.

BACKGROUND OF THE INVENTION

1. Field of the Invention

The present invention relates to an endoscope apparatus including a first optical system for observing an inside of an object and a second optical system for observing the inside of the object, the second optical system providing parallax relative to the first optical system, inside an insertion portion of an endoscope.

2. Description of the Related Art

As is well known, endoscopes are widely used in a medical field and an industrial field. In the case of endoscopes used in the medical field, an elongated insertion portion is inserted to the inside of a body cavity, which is a subject, enabling observation of an organ inside the body cavity and, as necessary, provision of various treatments using a treatment instrument inserted into a treatment instrument insertion channel.

In the case of endoscopes used in the industrial field, an elongated insertion portion is inserted to, e.g., the inside of a jet engine, a piping of a plant or the inside of a machine, which is an object, enabling, e.g., observation and/or various treatments of, e.g., damage and corrosion inside the object.

Also, the configuration in which an image pickup unit that includes an image pickup device including, e.g., an observation optical system and a CCD is provided inside a distal end portion positioned on the distal end side in an insertion direction (hereinafter simply referred to as "distal end side") of an insertion portion of an endoscope is known.

Here, for example, in observation of the inside of an object using an industrial endoscope, as a technique that quantitatively measures an observed site such as a damage, a defect or a failed part inside a machine, what is called stereoscopic measurement in which an image of a same site is picked up in two directions that provide parallax, a correlative operation of the two picked-up still images exhibiting parallax is performed to obtain an amount of displacement of a measurement point in each of the images, and, e.g., a size and/or a depth of the observed site is quantitatively measured from the displacement amounts using the known principle of triangulation is publicly known.

For example, Japanese Patent No. 4750175 discloses a configuration of a stereoscopic observation apparatus in which in a distal end portion of an insertion portion, a first optical system and a second optical system providing parallax relative to the first optical system are provided side by side, an image pickup device is provided on the rear side of the first optical system and the second optical system in an insertion direction (hereinafter simply referred to as "rear side"), a light-blocking shutter, which serves as time-difference optical path dividing/switching means for allowing a first light flux passed through the first optical system and a second light flux passed through the second optical system to individually enter an entire light-receiving surface of the image pickup device with a time difference is provided between the first and second optical systems and the image pickup device in the insertion direction, e.g., a size and/or a depth of an observed site is measured with high accuracy using a first image of the observed site formed on the entire light-receiving surface via the first optical system and a second image of the observed site formed on the entire light-receiving surface via the second optical system with a time difference from the first image, the time difference being provided by the light-blocking shutter, the second image exhibiting parallax relative to the first image.

SUMMARY OF THE INVENTION

An endoscope apparatus according to an aspect of the present invention includes: a first optical system for observing an inside of an object, the first optical system being provided in an insertion portion of an endoscope to be inserted to the object; a second optical system for observing the inside of the object, the second optical system being provided in the insertion portion and providing parallax relative to the first optical system; a light-blocking shutter that is pivotable between a first position in which the light-blocking shutter blocks a first optical path of the first optical system and a second position in which the light-blocking shutter blocks a second optical path of the second optical system, a magnetic body being formed on at least a part of the light-blocking shutter or at least a part of the light-blocking shutter includes a magnetic body; a magnet rotor fixed to a pivot shaft of the light-blocking shutter; a drive coil that upon direct current being provided to the drive coil, provides a magnetic force to the magnet rotor to pivot the light-blocking shutter from the first position to the second position or from the second position to the first position; a detection coil provided in a pivoting region of pivoting of the magnetic body along with pivoting of the light-blocking shutter, alternating current being provided to the detection coil; an image pickup device that individually forms a first image of an observed site of the object observed via the first optical system and a second image of the observed site observed via the second optical system, the second image exhibiting parallax relative to the first image, on an entire light-receiving surface with a time difference provided by the light-blocking shutter; and a control section provided inside the endoscope or an apparatus body to which the endoscope is connected, the control section performing measurement of the observed site from the first image and the second image formed on the light-receiving surface of the image pickup device, wherein the control section performs control to provide the direct current to the drive coil and performs control to provide the alternating current to the detection coil, and where the alternating current is provided to the detection coil, the control section detects a pivotal position of the light-blocking shutter by detecting variation of an inductance when a magnetic field generated in a hollow portion of the detection coil is blocked by the magnetic body, from a value of the alternating current.

DETAILED DESCRIPTION OF THE PREFERRED EMBODIMENTS

Embodiments of the present invention will be described below with reference to the drawings. Note that in the below, each of endoscope apparatuses will be described taking an industrial endoscope apparatus as an example.

First Embodiment

Figure 1:
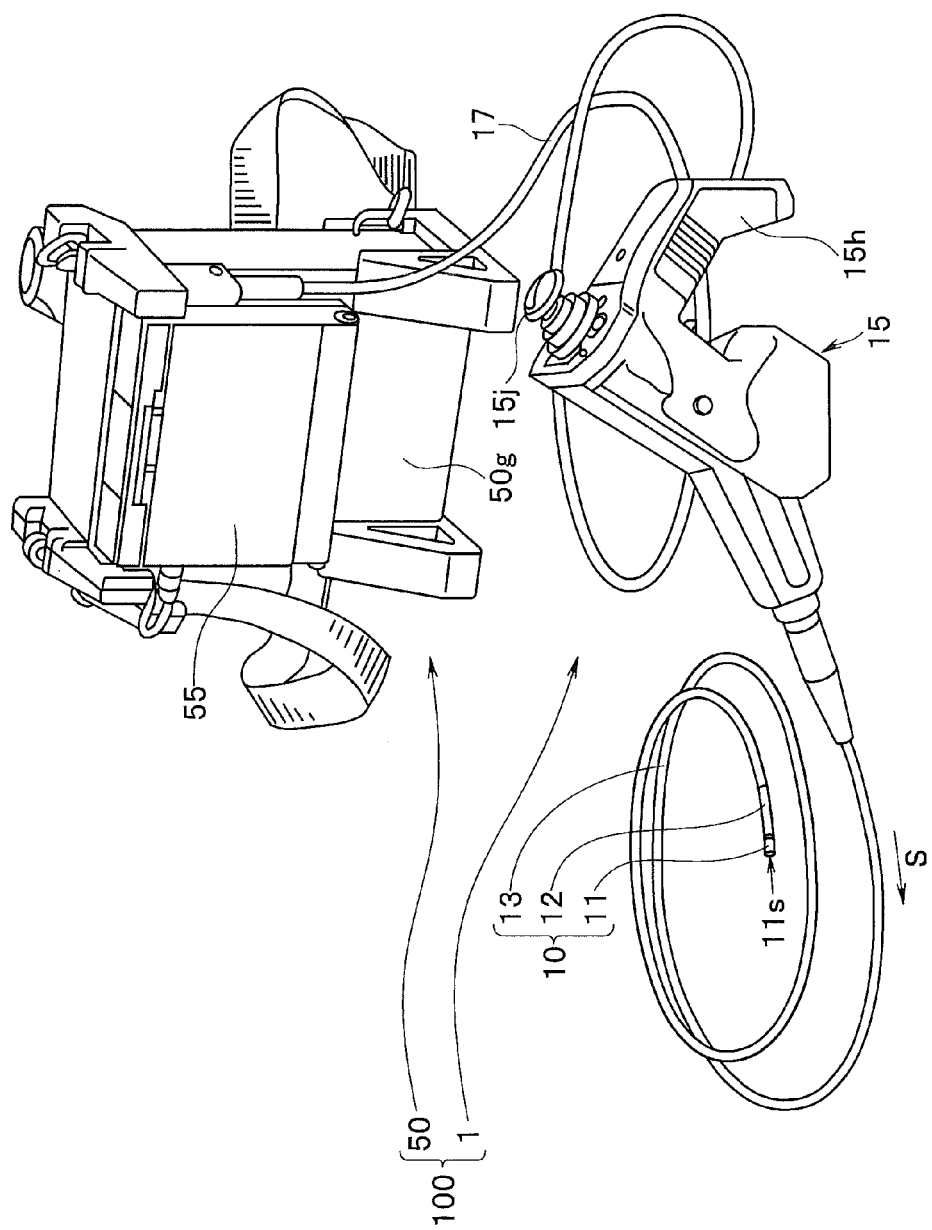
FIG. 1 is a perspective view of an endoscope apparatus according to a first embodiment.

FIG. 1 is a perspective view of an endoscope apparatus according to the present embodiment.

As illustrated in FIG. 1, a major part of an endoscope apparatus 100 includes an endoscope 1 and an apparatus body 50 connected to the endoscope 1.

A major part of the endoscope 1 includes: an elongated and flexible insertion portion 10; an operation portion 15 connected to a proximal end in an insertion direction S (hereinafter simply referred to as "proximal end") of the insertion portion 10, the operation portion 15 including a grasping section 15h, and a universal cord 17 extending from the grasping section 15h of the operation portion 15.

In the insertion portion 10, a distal end portion 11, a bending portion 12, which is bendable, for example, in four directions, upward, downward, leftward and rightward, by means of operation of a joystick 15j provided at the operation portion 15, and a long flexible tube portion 13, which includes a flexible member, are provided so as to be continuous in this order from the distal end side of the insertion portion 10, and a proximal end of the flexible tube portion 13 is connected to the operation portion 15.

Note that at the operation portion 15, in addition to the joystick 15j, e.g., non-illustrated various switches for providing image pickup operation instructions to a later-described image pickup unit 25 (see FIG. 2) provided in the distal end portion 11 and a later-described measurement switch 15i (see FIG. 6) are provided. Note that the measurement switch 15i may be provided at an apparatus body 50.

The apparatus body 50 has, for example, a box shape, and a monitor 55 that displays an endoscopic image picked up by the image pickup unit 25 of the endoscope 1 is fixed to an exterior housing 50g formed by means of, for example, magnesium die casting, for example, in such a manner that the monitor 55 can be opened/closed relative to the exterior housing 50g. Note that the monitor 55 may be attachable/detachable to/from the exterior housing 50g or may be fixed with a monitor surface consistently exposed.

Next, a configuration of the image pickup unit provided inside the distal end portion 11 will be described with reference to FIGS. 2 to 5.

Figure 2:
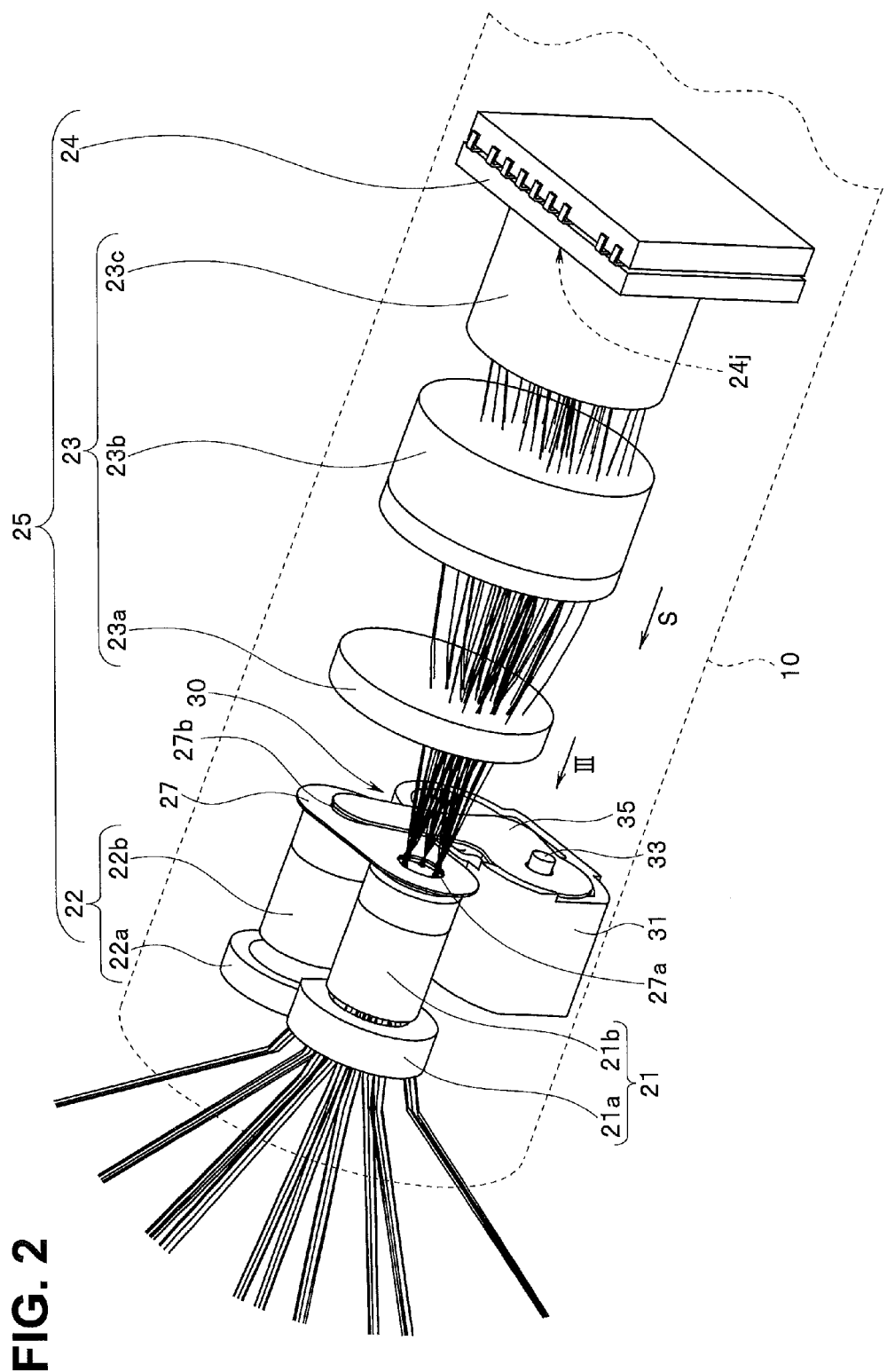
FIG. 2 is a perspective view of an image pickup unit provided inside the distal end portion in FIG. 1.
Figure 3:
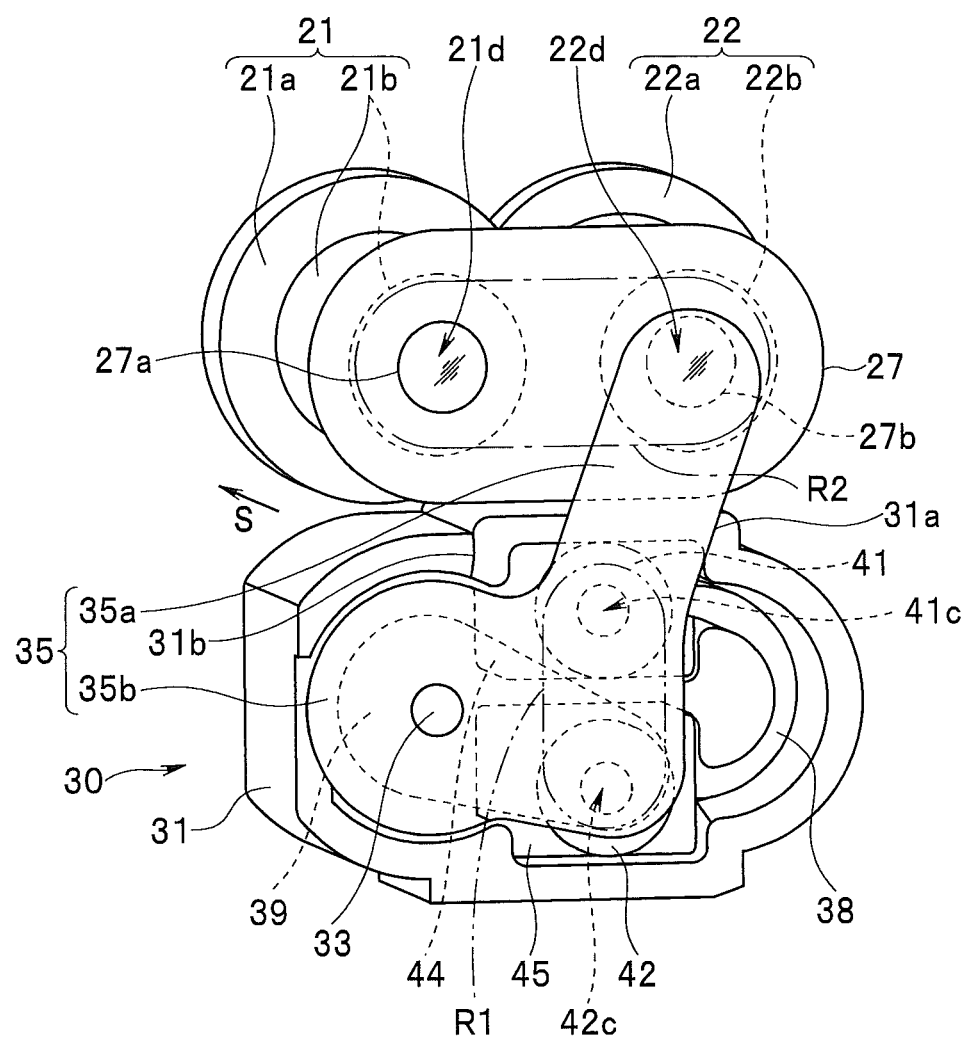
FIG. 3 is a perspective view illustrating an actuator unit in the image pickup unit in FIG. 2 together with a first optical system, a second optical system and a diaphragm plate as viewed in the III direction in FIG. 2.

FIG. 2 is a perspective view of the image pickup unit provided inside the distal end portion in FIG. 1, and FIG. 3 is a perspective view illustrating an actuator unit in the image pickup unit in FIG. 2 together with a first optical system, a second optical system and a diaphragm plate as viewed in the III direction in FIG. 2.

Figure 4:
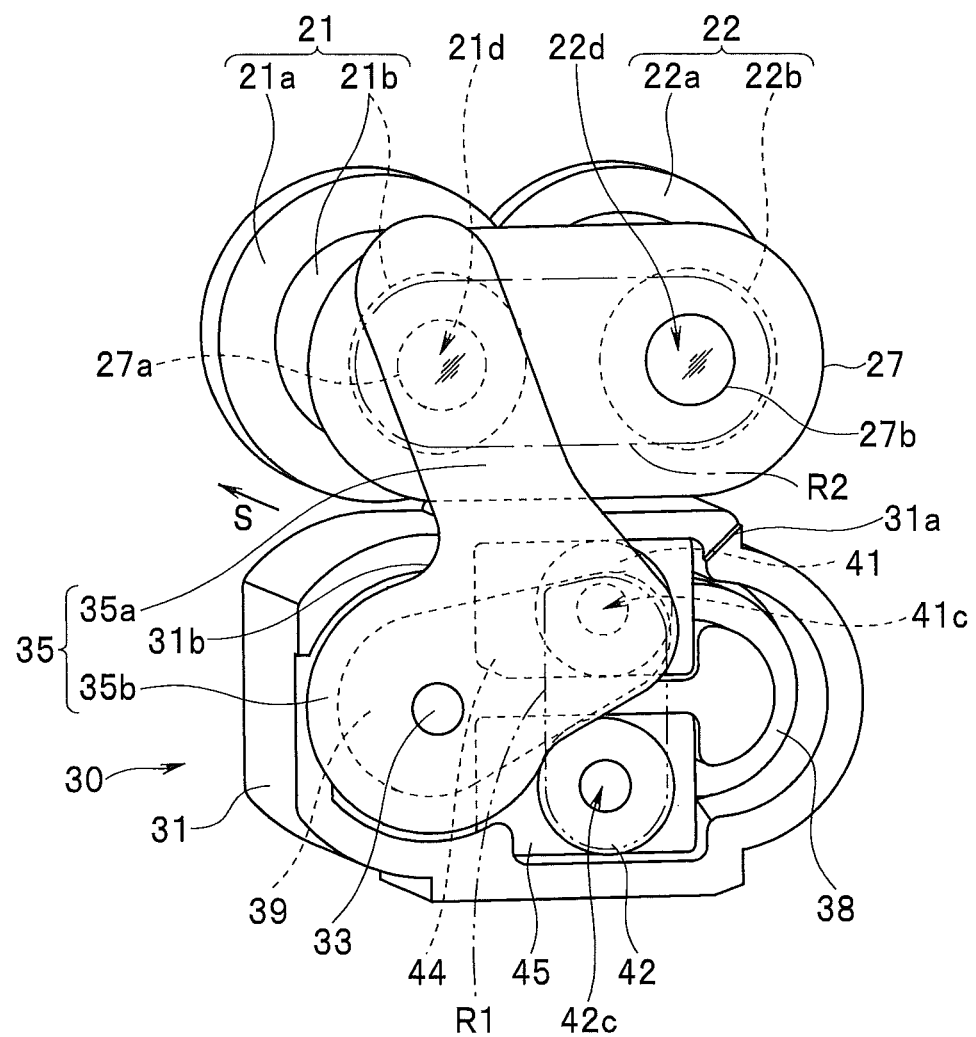
FIG. 4 is a perspective view illustrating the actuator unit in which a first optical path of the first optical system in FIG. 3 is blocked by a light-blocking shutter, together with the first optical system, the second optical system and the diaphragm plate.
Figure 5:
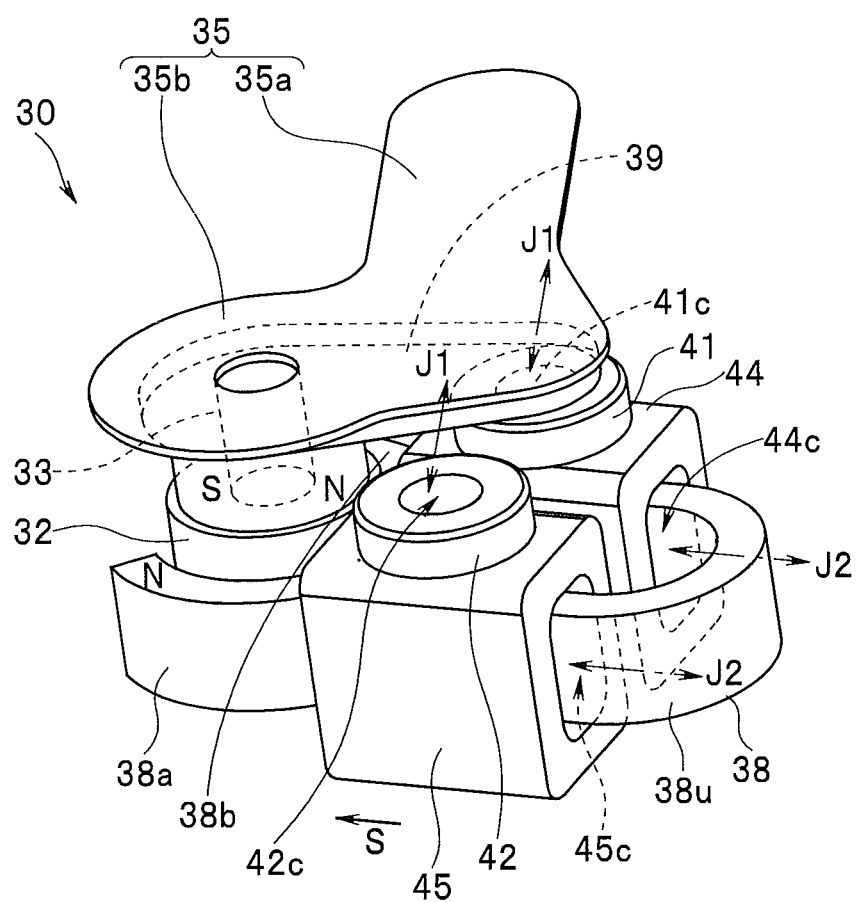
FIG. 5 is an enlarged perspective view of the actuator unit in FIGS. 3 and 4.

FIG. 4 is a perspective view illustrating the actuator unit in which a first optical path of the first optical system in FIG. 3 is blocked by a light-blocking shutter, together with the first optical system, the second optical system and the diaphragm plate, and FIG. 5 is an enlarged perspective view of the actuator unit in FIGS. 3 and 4.

As illustrated in FIG. 2, the image pickup unit 25 is provided inside the distal end portion 11. More specifically, the image pickup unit 25 includes a first optical system 21 for observing the inside of an object, a second optical system 22 for observing the inside of the object, the second optical system 22 providing parallax relative to the first optical system 21, and a diaphragm plate 27.

The first optical system 21 includes an objective lens 21a, and a lens group 21b positioned on the rear side relative to the objective lens 21a, and is provided in such a manner that the objective lens 21a is exposed in a distal end face 11s (see FIG. 1) of the distal end portion 11.

The second optical system 22 includes an objective lens 22a, and a lens group 22b positioned on the rear side relative to the objective lens 22a, and is provided side-by-side with the first optical system 21 inside the distal end portion 11 in such a manner that the objective lens 22a is exposed in the distal end face 11s.

The diaphragm plate 27 is attached to proximal end faces of the lens group 21b and the lens group 22b. In the diaphragm plate 27, a diaphragm aperture 27a that narrows down a first light flux passed through the first optical system 21 and a diaphragm aperture 27b that narrows down a second light flux passed through the second optical system 22 are formed.

Also, the image pickup unit 25 includes a rear lens group 23 including lenses 23a, 23b and 23c on the rear side of the diaphragm plate 27, and an image pickup device 24 on the rear side of the lens 23c.

The image pickup device 24 is intended to, according to the drive control performed by a later-described CPU 80 (see FIG. 6), form a first image of an observed site of an object observed via the first optical system 21, the diaphragm aperture 27a and the rear lens group 23, and a second image of the observed site of the object observed via the second optical system 22, the diaphragm aperture 27b and the rear lens group 23, the second image exhibiting parallax relative to the first image, on an entire light-receiving surface 24j with a time difference of, for example, 1/30 seconds provided by a light-blocking shutter 35 described later, thereby picking up the first image and the second image, individually.

The image pickup unit 25 also includes an actuator unit 30 positioned adjacent to the first optical system 21 and the second optical system 22, below the first optical system 21 and the second optical system 22.

As illustrated in FIGS. 3 to 5, a major part of the actuator unit 30 includes a holding member 31, a magnet rotor 32, a pivot shaft 33, the light-blocking shutter 35, a yoke 38, detection coils 41 and 42, and drive coils 44 and 45.

As illustrated in FIG. 2, the holding member 31 is positioned adjacent to the first optical system 21 and the second optical system 22, below the first optical system 21 and the second optical system 22, and includes, inside, the pivot shaft 33, the magnet rotor 32, a later-described fixed portion 35b of the light-blocking shutter 35, the yoke 38, the detection coils 41 and 42 and the drive coils 44 and 45.

As illustrated in FIGS. 3 to 5, the pivot shaft 33 is pivotally held by the holding member 31, and the ring-shaped magnet rotor 32 with an N pole formed in one half portion and an S pole formed in the other half portion is fixed to an outer periphery on the distal end side of the pivot shaft 33. In other words, the magnet rotor 32 pivots integrally with the pivot shaft 33.

The fixed portion 35b of the light-blocking shutter 35 is fixed to a proximal end of the pivot shaft 33. The light-blocking shutter 35 is formed in a thin-plate shape using a non-magnetic body, and a major part of the light-blocking shutter 35 includes a light-blocking portion 35a and the fixed portion 35b. As a result of the fixed portion 35b being fixed to the proximal end of the pivot shaft 33, the fixed portion 35b is pivotable together with the pivot shaft 33.

More specifically, the light-blocking shutter 35 is pivotable between the first position illustrated in FIG. 4 in which the light-blocking portion 35a blocks a first optical path 21d of the first optical system 21 and the second position illustrated in FIG. 3 in which the light-blocking portion 35a blocks a second optical path 22d of the second optical system 22. The first position is defined by the light-blocking shutter 35 abutting against a stopper 31b of the holding member 31, and the second position is defined by the light-blocking shutter 35 abutting against a stopper 31a of the holding member 31.

Also, a magnetic body 39 is provided on a surface of the fixed portion 35b of the light-blocking shutter 35, the surface facing the detection coils 41 and 42. Note that the magnetic body 39 may be formed integrally with the fixed portion 35b.

As illustrated in FIG. 5, the yoke 38 includes a ferromagnetic body. The yoke 38 includes a U-shaped portion 38u having a U-shape, the U-shaped portion 38u being positioned on the proximal end side in an insertion direction S (hereinafter simply referred to as "proximal end side") and extending through hollow portions 44c and 45c of the drive coils 44 and 45, and also includes, on the distal end side, a yoke 38a covering one side of an outer periphery of the magnet rotor 32 and a yoke 38b facing the yoke 38a and covering the other side of the outer periphery of the magnet rotor 32.

Upon direct current being provided to the drive coils 44 and 45, magnetic fields are generated and the yokes 38a and 38b thereby serve as magnetic poles that are opposite to each other. In other words, if the yoke 38a serves as an N pole, the yoke 38b serves as an S pole, and if the yoke 38a serves as an S pole, the yoke 38b serves an N pole. Note that directions of the magnetic fields generated in the yokes 38a and 38b are reversed depending on a direction of the direct current provided to the drive coils 44 and 45.

Therefore, for example, when the yoke 38a serves as an N pole and the yoke 38b serves as an S pole, if the S pole of the magnet rotor 32 is positioned on the side facing the yoke 38a and the N pole of the of the magnet rotor 32 is positioned on the side facing the yoke 38b, the respective N poles and S poles attract each other, and the magnet rotor 32, that is, the pivot shaft 33 thereby rotates. The rotation of the light-blocking shutter 35 is continued until the light-blocking shutter 35 abuts against the stopper 31a. Here, the light-blocking shutter 35 does not rotate to a position where the respective N poles and S poles rightly face each other but rotates to a position defined by the stopper 31a.

Also, for example, when the yoke 38a serves as an N pole and the yoke 38b serves as an S pole, if the N pole of the magnet rotor 32 is positioned on the side facing the yoke 38a and the S pole of the magnet rotor 32 is positioned on the side facing the yoke 38b, the N pole and the N pole repel each other, and the S pole and the S pole also repel each other, and the magnet rotor 32, that is, the pivot shaft 33 thereby rotates until the respective N poles and S poles attract each other. The rotation of the light-blocking shutter 35 is continued until the light-blocking shutter 35 abuts against the stopper 31b. Here, the light-blocking shutter 35 does not rotate to a position where the respective N poles and S poles rightly face each other, but rotates to a position defined by the stopper 31b.

Consequently, the light-blocking portion 35a of the light-blocking shutter 35 fixed to the pivot shaft 33 is pivotable between the first position and the second position. Note that a direction of pivoting of the pivot shaft 33 changes depending on the direction of the direct current provided to the drive coils 44 and 45. Also, the light-blocking portion 35a does not rotate to a position in which the respective N pole and S poles face each other, but is fixed by the stopper 31a or 31b. Therefore, for example, when the yoke 38a changes from an N pole to an S pole, the switching of the light-blocking shutter 35 is easy compared to a case where the light-blocking shutter 35 is located at a position in which the respective N poles and S poles face each other. However, the light-blocking shutter 35 may rotate to a position in which the respective N poles and S poles face each other.

As illustrated in FIGS. 3 to 5, the drive coils 44 and 45 are intended to, upon direct current being provided from a later-described direct current power supply circuit section 81

(see FIG. 6) according to the drive control performed by the later-described CPU 80 (see FIG. 6), provide a magnetic force to the magnet rotor 32 via the yoke 38 to pivot the light-blocking shutter 35 from the first position to the second position or pivot the light-blocking shutter 35 from the second position to the first position, and are provided side by side inside the holding member 31.

Also, as illustrated in FIGS. 3 to 5, the detection coils 41 and 42 are provided side by side in a pivoting region R1 of pivoting of a magnetic body 39 along with pivoting of the light-blocking shutter 35. More specifically, the detection coil 41 is fixed in abutment with an upper face of the drive coil 44, and the detection coil 42 is fixed in abutment with an upper face of the drive coil 45. Note that the detection coils 41 and 42 are provided side-by-side in such a manner that at least hollow portions 41c and 42c are positioned in the pivoting region R1.

Furthermore, the detection coils 41 and 42 are provided side by side with the drive coils 44 and 45 so that a magnetic field direction J1 in the hollow portions 41c and 42c of the detection coils 41 and 42 and a magnetic field direction J2 in the hollow portions 44c and 45c of the drive coils 44 and 45 are perpendicular to each other.

As illustrated in FIG. 4, the detection coil 41 is provided at a position where the hollow portion 41c is blocked by the magnetic body 39 in the aforementioned first position, and as illustrated in FIG. 3, the detection coil 42 is provided at a position where the hollow portion 42c is blocked by the magnetic body 39 in the aforementioned second position.

In other words, the magnetic body 39 is formed so as to have a size and a shape that allow the magnetic body 39 to block the hollow portion 41c of the detection coil 41 and release the hollow portion 42c of the detection coil 42 when the light-blocking shutter 35 is moved to the first position as illustrated in FIG. 4, and block the hollow portion 42c and releases the hollow portion 41c when the light-blocking shutter 35 is moved to the second position illustrated in FIG. 3.

The light-blocking portion 35a of the light-blocking shutter 35 is formed so as to have a shape and a size that allows the light-blocking portion 35a to block the first optical path 21d when the magnetic body 39 blocks the hollow portion 41c, and block the second optical path 22d when the magnetic body 39 blocks the hollow portion 42c.

The detection coil 41 is formed so as to have a larger number of coil element wire turns than the number of coil element wire turns of the detection coil 42.

The detection coils 41 and 42 are used to detect movement of the light-blocking shutter 35 by detecting, based on variation in alternating current value, whether or not the magnetic body 39 blocks the hollow portion 41c or 42c as a result of alternating current being provided from the later-described alternating current power supply circuit section 82 (see FIG. 6) according to the drive control performed by the later-described CPU 80 (see FIG. 6).

Next, a circuit that moves the light-blocking shutter 35 and detects the movement will be described with reference to FIG. 6 and FIG. 7. FIG. 6 is a block diagram schematically illustrating a circuit in the endoscope apparatus in FIG. 1, the circuit moving the light-blocking shutter in FIG. 5 and detecting the movement, and FIG. 7 is a graphic chart indicating inductance variation detected by the inductance detection section in FIG. 6 along with movement of the light-blocking shutter in FIG. 2, between the first position and the second position.

Figure 6:
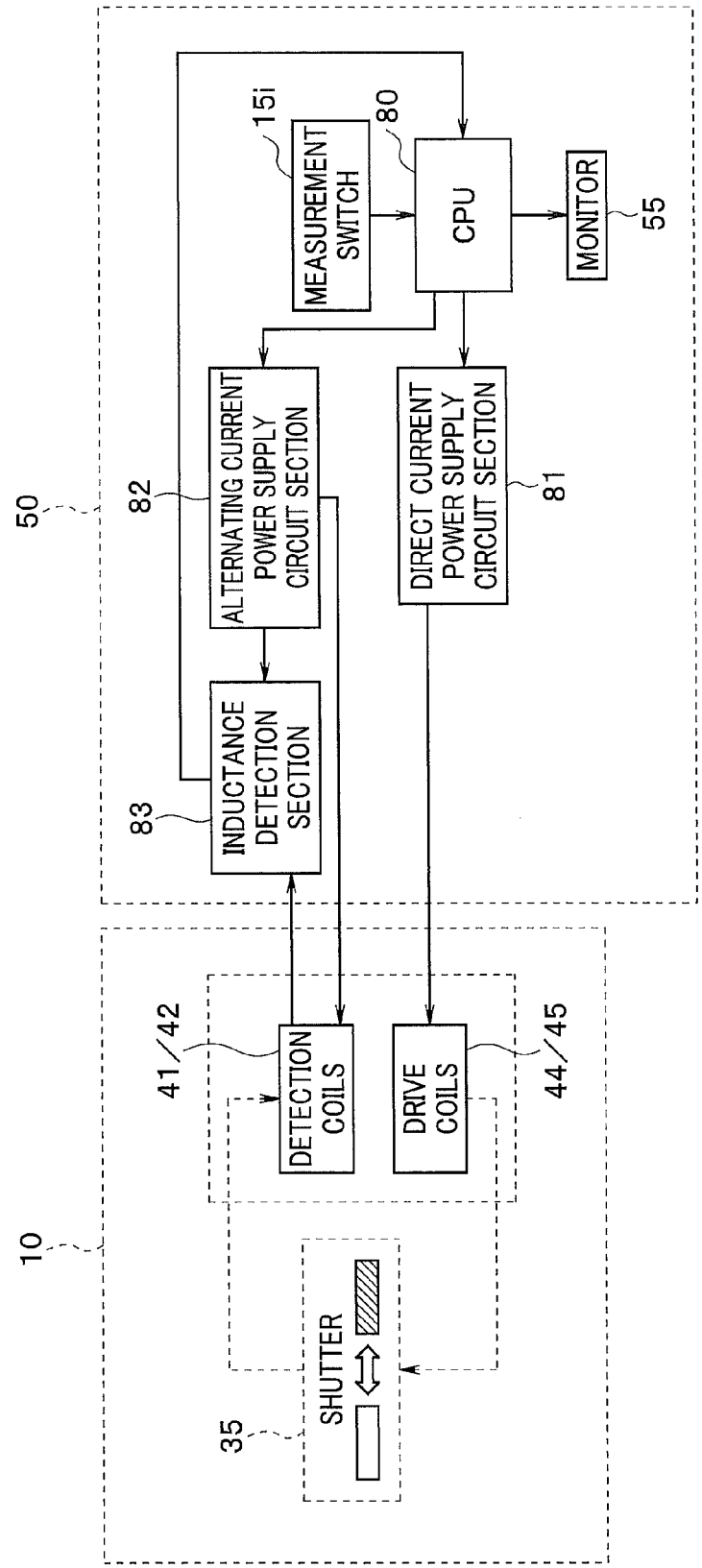
FIG. 6 is a block diagram schematically illustrating a circuit in the endoscope apparatus in FIG. 1, the circuit moving the light-blocking shutter in FIG. 5 and detecting the movement.
Figure 7:
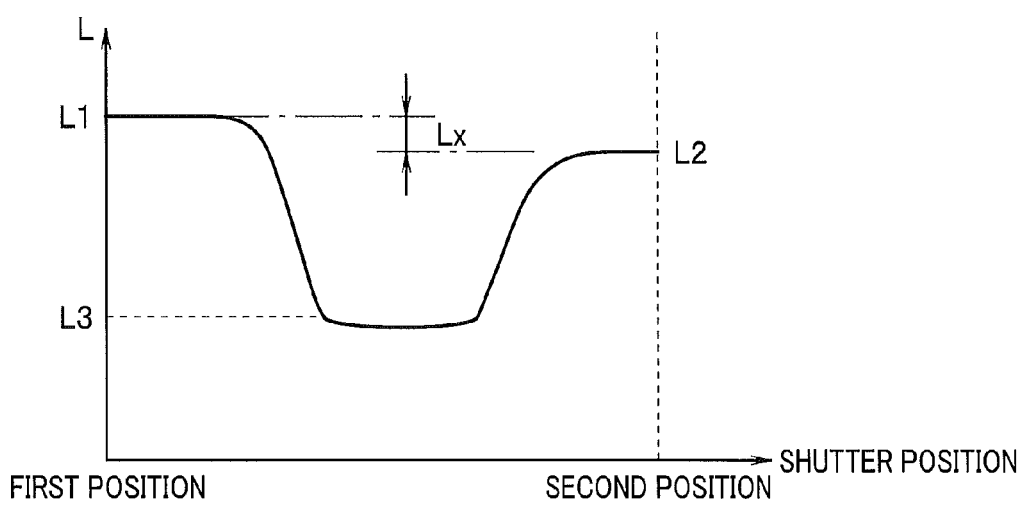
FIG. 7 is a graphic chart indicating inductance variation detected by the inductance detection section in FIG. 6 along with movement of the light-blocking shutter in FIG. 2, between a first position and a second position.

As illustrated in FIG. 6, the endoscope apparatus 100 includes, inside the apparatus body 50, the CPU 80, which is a control section, the direct current power supply circuit section 81, which is a direct current power supply, an alternating current power supply circuit section 82, which is an alternating current power supply, and an inductance detection section 83. Note that the CPU 80, the direct current power supply circuit section 81, the alternating current power supply circuit section 82 and the inductance detection section 83 may be provided inside the endoscope 1.

The direct current power supply circuit section 81 is electrically connected to the CPU 80 and the drive coils 44 and 45, and is intended to provide direct current to the drive coils 44 and 45 according to the drive control performed by the CPU 80.

The alternating current power supply circuit section 82 is electrically connected to the CPU 80, the detection coils 41 and 42 and the inductance detection section 83, and is intended to provide alternating current to the detection coils 41 and 42 according to the drive control performed by the CPU 80.

Note that the alternating current power supply circuit section 82 may be configured to consistently provide alternating current to the detection coils 41 and 42 when power of the endoscope apparatus 100 is on or may be configured to provide alternating current only when a pivotal position of the light-blocking shutter 35 is detected.

The inductance detection section 83 is electrically connected to the detection coils 41 and 42, the alternating current power supply circuit section 82 and the CPU 80, and is intended to detect variation of a later-described inductance L (see FIG. 7) occurring when the magnetic body 39 blocks each of the hollow portions 41c and 42c of the detection coils 41 and 42 according to the drive control performed by the CPU 80.

In addition to the direct current power supply circuit section 81, the alternating current power supply circuit section 82 and the inductance detection section 83, the measurement switch 15i and the monitor 55 are electrically connected to the CPU 80.

When the measurement switch 15i is turned on by an operator, the CPU 80 performs control to provide direct current to the drive coils 44 and 45 via the direct current power supply circuit section 81 to move the light-blocking shutter 35 to the second position and thereby form the aforementioned first image on the light-receiving surface 24j of the image pickup device 24, and then move the light-blocking shutter 35 to the first position and thereby form the second image on the light-receiving surface 24j, and measure, e.g., a size and a depth of the aforementioned observed site from the first image and the second image, which are still images picked up with the time difference, using the above-described method.

Also, the CPU 80 performs control to provide alternating current to the detection coils 41 and 42 via the alternating current power supply circuit section 82 to detect variation of the inductance L when the magnetic field generated in each of the hollow portions 41c and 42c is blocked by the magnetic body 39, from a value of the alternating current via the inductance detection section 83 and thereby detect pivotal movement of the light-blocking shutter 35.

More specifically, as illustrated in FIG. 7, the CPU 80 detects a difference Lx between values L1 and L2 of inductances L due to the difference in number of turns between the respective detection coils 41 and 42, the inductances L being generated as a result of the magnetic body 39 blocking the magnetic fields in the hollow portions 41c and 42c of the detection coils 41 and 42 along with pivoting of the light-blocking shutter 35 in the first position and the second position, respectively, via the inductance detection section 83, and thereby detects that the light-blocking shutter 35 is moved from the first position to the second position or is moved from the second position to the first position.

In other words, after movement of the light-blocking shutter 35, if it is detected that the value of the inductance L is increased by Lx to L1, the CPU 80 detects that the light-blocking shutter 35 is moved to the first position in which the magnetic body 39 blocks the hollow portion 41c and the light-blocking portion 35a blocks the first optical path 21d as illustrated in FIG. 4, and if it is detected that the value of the inductance L is decreased by Lx to L2, the CPU 80 detects that the light-blocking shutter 35 is moved to the second position in which the magnetic body 39 blocks the hollow portion 42c and the light-blocking portion 35a blocks the second optical path 22d as illustrated in FIG. 3.

Also, as illustrated in FIG. 7, the CPU 80 detects L3, which is a value of the inductance L generated as a result of the magnetic body 39 releasing magnetic fields in the hollow portions 41c and 42c of the respective detection coils 41 and 42 along with pivoting of the light-blocking shutter 35, which is substantially lower than L1 and L2, via the inductance detection section 83, and thereby detects that the light-blocking shutter 35 is located between the first position and the second position.

Furthermore, if the CPU 80 cannot detect variation of the inductance L even though direct current is provided to the drive coils 44 and 45 during alternating current being provided to the respective detection coils 41 and 42, the CPU 80 detects that the light-blocking shutter 35 is in a non-moving state via the inductance detection section 83, and performs control to provide a warning via, for example, the monitor 55, the warning indicating that measurement values of the observed site obtained via the image pickup device 24 are incorrect values obtained from two images picked up with a time difference via a same optical system as a result of movement of the distal end portion 11 as mentioned above. Note that the warning is not limited to display and may be, e.g., sound.

Next, operation of the present embodiment will be described.

First, in a state in which the control performed by the CPU 80 to provide direct current to the drive coils 44 and 45 is stopped, when the magnetic body 39 illustrated in FIG. 4 blocks the hollow portion 41c and the light-blocking portion 35a is moved to the first position in which the light-blocking portion 35a blocks the first optical path 21d, as described above, the light-blocking shutter 35 is prevented by the stopper 31b provided at the holding member 31 from rotating beyond the first position in one direction. Note that when the drive control to provide direct current to the drive coils 44 and 45 is stopped, the yoke 38 acts as a ferromagnetic body, a pole on the side close to the yoke from among the N pole and the S pole of the magnet rotor is attracted to the yoke 38. Therefore, in this case, attraction between the yoke 38a and the N pole of the magnet rotor 32 and attraction between the N pole of the yoke 38b and the S pole of the magnet rotor 32 are maintained, and the light-blocking shutter 35 is thus prevented from being moved from the first position.

In the first position, if an operator turns on the measurement switch 15i, the CPU 80 performs control to drive the direct current power supply circuit section 81 to provide direct current to the drive coils 44 and 45, and performs control to drive the alternating current power supply circuit section 82 to provide alternating current to the detection coils 41 and 42. The CPU 80 detects that the value of the inductance L is L1 as a result of the magnetic body 39 blocking the hollow portion 41c and releasing the hollow portion 42c, from a current value of the alternating current via the inductance detection section 83. Therefore, the CPU 80 detects that the light-blocking shutter 35 is in the first position. Note that the CPU 80 may cause the monitor 55 to provide display indicating that the light-blocking shutter 35 is in the first position.

Note that if the control performed by the CPU 80 to provide direct current to the drive coils 44 and 45 is stopped by, e.g., a foreign object, when the operator turns on the measurement switch 15i in a state in which the light-blocking shutter 35 is located between the first position and the second position, that is, the light-blocking portion 35a blocks neither the first optical path 21d nor the second optical path 22d, the CPU 80 performs control to drive the direct current power supply circuit section 81 to provide the direct current to the drive coils 44 and 45, and performs control to drive the alternating current power supply circuit section 82 to provide alternating current to the detection coils 41 and 42.

Here, since the magnetic body 39 blocks neither of the hollow portions 41c and 42c, as illustrated in FIG. 7, as the inductance L detected via the inductance detection section 83, a value L3, which is substantially lower than those in the first position and the second position, is detected, and the CPU 80 detects that the light-blocking shutter 35 is located between the first position and the second position, via the inductance detection section 83, and the CPU 80 causes the monitor 55 to display a warning.

Next, when the light-blocking shutter 35 is moved from the first position to the second position, as a result of direct current being provided to the drive coils 44 and 45, for example, the yoke 38a of the yoke 38 serves as an N pole and the yoke 38b serves as an S pole.

As a result, the N pole of the magnet rotor 32 repels the N pole of the yoke 38a, and the S pole of the magnet rotor repels the S pole of the yoke 38b, and subsequently, the S pole of the magnet rotor 32 attracts the N pole of the yoke 38a, and the N pole of the magnet rotor attracts the S pole of the yoke 38b, and the magnet rotor 32 thereby rotates in the other direction.

Consequently, in the light-blocking shutter 35, the magnetic body 39 illustrated in the FIG. 3 blocks the hollow portion 42c, and the light-blocking portion 35a is moved to the second position where the light-blocking portion 35a blocks the second optical path 22d. Note that the light-blocking shutter 35 is prevented by the stopper 31a provided at the holding member 31 from rotating beyond the second position in the other direction.

Here, the CPU 80 detects decrease in the value of the inductance L from L1 to L2 as a result of the magnetic body 39 blocking the hollow portion 42c and releasing the hollow portion 41c, that is, the difference Lx, from variation in current value of the alternating current via the inductance detection section 83. Thus, the CPU 80 detects that the light-blocking shutter 35 is moved to the second position. Note that the CPU 80 may cause the monitor 55 to provide display indicating that the light-blocking shutter 35 is moved to the second position.

Note that, if there is no variation in value of the inductance L, the CPU 80 detects that the light-blocking shutter 35 is not moved to the second position, and causes the monitor 55 to display a warning.

After the light-blocking shutter 35 is moved to the second position, a first light flux passed through the first optical path 21d forms an image on the light-receiving surface 24j of the image pickup device 24 via the first optical system 21, the diaphragm aperture 27a and the rear lens group 23, whereby a first image is picked up.

After the light-blocking shutter 35 is moved to the second position, the CPU 80 stops the control to provide direct current to the drive coils 44 and 45. Note that upon the stoppage of the drive control to provide direct current to the drive coils 44 and 45, the yoke 38b acts as a ferromagnetic body, a pole on the side close to the yoke from among the N pole and the S pole of the magnet rotor is attracted to the yoke. Therefore, in this case, attraction between the N pole of the yoke 38a and the S pole of the magnet rotor 32 and attraction between the S pole of the yoke 38b and the N pole of the magnet rotor 32 are maintained, and the light-blocking shutter 35 is thus prevented from being moved from the second position.

Next, when light-blocking shutter 35 is moved from the second position to the first position, direct current having a direction opposite to the direction when the light-blocking shutter 35 is moved from the first position to the second position is provided to the drive coils 44 and 45, whereby, for example, the yoke 38a of the yoke 38 serves as an S pole and the yoke 38b serves as an N pole.

As a result, the S pole of the magnet rotor 32 repels the S pole of the yoke 38a and the N pole of the magnet rotor repels the N pole of the yoke 38b, and subsequently, the N pole of the magnet rotor 32 attracts the S pole of the yoke 38a and the S pole of the magnet rotor attracts the N pole of the yoke 38b, whereby the magnet rotor 32 rotates in the one direction.

Consequently, the light-blocking shutter 35 is moved to the first position in which the magnetic body 39 illustrated in FIG. 4 blocks the hollow portion 41c and the light-blocking portion 35a blocks the first optical path 21d. Note that the light-blocking shutter 35 is prevented by the stopper 31b provided at the holding member 31 from rotating beyond the first position in the one direction.

Here, the CPU 80 detects increase in value of the inductance L from L2 to L1 as a result of the magnetic body 39 blocking the hollow portion 41c and releasing the hollow portion 42c, that is, the difference Lx, from variation in current value of the alternating current via the inductance detection section 83. Thus, the CPU 80 detects that the light-blocking shutter 35 is moved to the first position. Note that the CPU 80 may cause the monitor 55 to provide display indicating that the light-blocking shutter 35 is moved to the first position.

Note that, if there is no variation in value of the inductance L, the CPU 80 detects that the light-blocking shutter 35 is not moved to the first position, and causes the monitor 55 to display a warning.

After the light-blocking shutter 35 is moved to the first position, a second light flux passed through the second optical path 22d forms an image on the light-receiving surface 24j of the image pickup device 24 via the second optical system 22, the diaphragm aperture 27b and the rear lens group 23, whereby a second image is picked up.

After the light-blocking shutter 35 is moved to the first position, the CPU 80 stops the control to provide direct current to the drive coils 44 and 45. Note that, as described above, upon the stoppage of the drive control to provide direct current to the drive coils 44 and 45, the yoke 38 acts as a ferromagnetic body, and a pole on the side close to the yoke from among the N pole and the S pole of the magnet rotor is attracted to the yoke. Therefore, in this case, attraction between the yoke 38a and the N pole of the magnet rotor 32 and attraction between the N pole of the yoke 38b and the S pole of the magnet rotor 32 are maintained, and the light-blocking shutter 35 is thus prevented from being moved from the first position.

Lastly, the CPU 80 performs measurement of the observed site from the first image and the second image, which are still images picked up by the image pickup device 24. Note that, although the above operation has been described taking, as an example, a case where a second image is picked up after a first image is picked up, it should be understood that a case opposite to this case may be employed.

As described above, the present embodiment indicates that movement of the light-blocking shutter 35 is detected using the detection coils 41 and 42.

More specifically, the present embodiment indicates that when direct current is provided to the drive coils 44 and 45 to move the light-blocking shutter 35 in a state in which alternating current is provided to the detection coils 41 and 42, if the magnetic body 39 blocks the hollow portion 41c, the CPU 80 detects that the light-blocking shutter 35 is moved to the first position in which the light-blocking shutter 35 blocks the first optical path 21d, by detecting the inductance L1 via the inductance detection section 83. Also, the present embodiment indicates that if the magnetic body 39 blocks the hollow portion 42c, the CPU 80 detects that the light-blocking shutter 35 is moved from the first position to the second position in which the light-blocking shutter 35 blocks the second optical path 22d, by detecting the inductance L2 via the inductance detection section 83 and detecting the difference Lx in the inductance L. Furthermore, the present embodiment indicates that if the magnetic body 39 blocks neither of the hollow portions 41c and 42c, the CPU 80 detects that the light-blocking shutter 35 is moved to a position between the first position and the second position in which the light-blocking shutter 35 blocks neither the first optical path 21d nor the second optical path 22d, by detecting the value L3, which is substantially lower than the L1 and L2 values of the inductance L, via the inductance detection section 83.

Furthermore, the present embodiment indicates that if the light-blocking shutter 35 is in a non-moving state despite of the CPU 80 performing the control to provide direct current to the drive coils 44 and 45, the CPU 80 causes the monitor 55 to display a warning.

Accordingly, if no warning is displayed on the monitor 55 after the measurement switch 15i is turned on, an operator can easily confirm that correct measurement of the observed site is performed from the first image picked up via the first optical path 21d and the second image picked up via the second optical path 22.

Also, detection of movement of the light-blocking shutter 35 can be performed using two detection coils 41 and 42 alone, enabling reduction in diameter and length in the insertion direction S of the distal end portion 11 including the actuator unit 30 therein compared to conventional cases where Hall elements are used.

Furthermore, the detection coils 41 and 42 can be arranged compactly by fixing the detection coils 41 and 42 in abutment with the respective upper faces of the drive coils 44 and 45 and making the magnetic field directions J1 and J2 be perpendicular to each other, enabling reduction in diameter and length in the insertion direction S of the distal end portion 11.

Furthermore, the actuator unit 30 is arranged compactly in a vacant space below the first optical system 21 and the second optical system 22 inside the distal end portion 11, enabling reduction in diameter and length in the insertion direction S of the distal end portion 11 compared to the conventional cases.

According to the above, the endoscope apparatus 100 including a configuration that enables highly-accurate and correct measurement of an observed site by means of reliable detection of movement of the light-blocking shutter 35 as well as reduction in diameter and length of the distal end portion 11 can be provided.

Note that a modification will be indicated below.

The present embodiment above indicates that since the number of coil element wire turns formed in the detection coil 41 is larger than that of the detection coil 42, the value L1 of the inductance L in the first position is larger by Lx than the value L2 of the inductance L in the second position, and based on this, the CPU 80 detects whether the light-blocking shutter 35 is moved to the first position or the second position.

The present invention is not limited to this case, and it is possible that: a same number of coil element wire turns is formed in each of the detection coils 41 and 42; and whether the light-blocking shutter 35 is moved to the first position or the second position is detected according to a direction of direct current provided to the drive coils 44 and 45.

Figure 8:
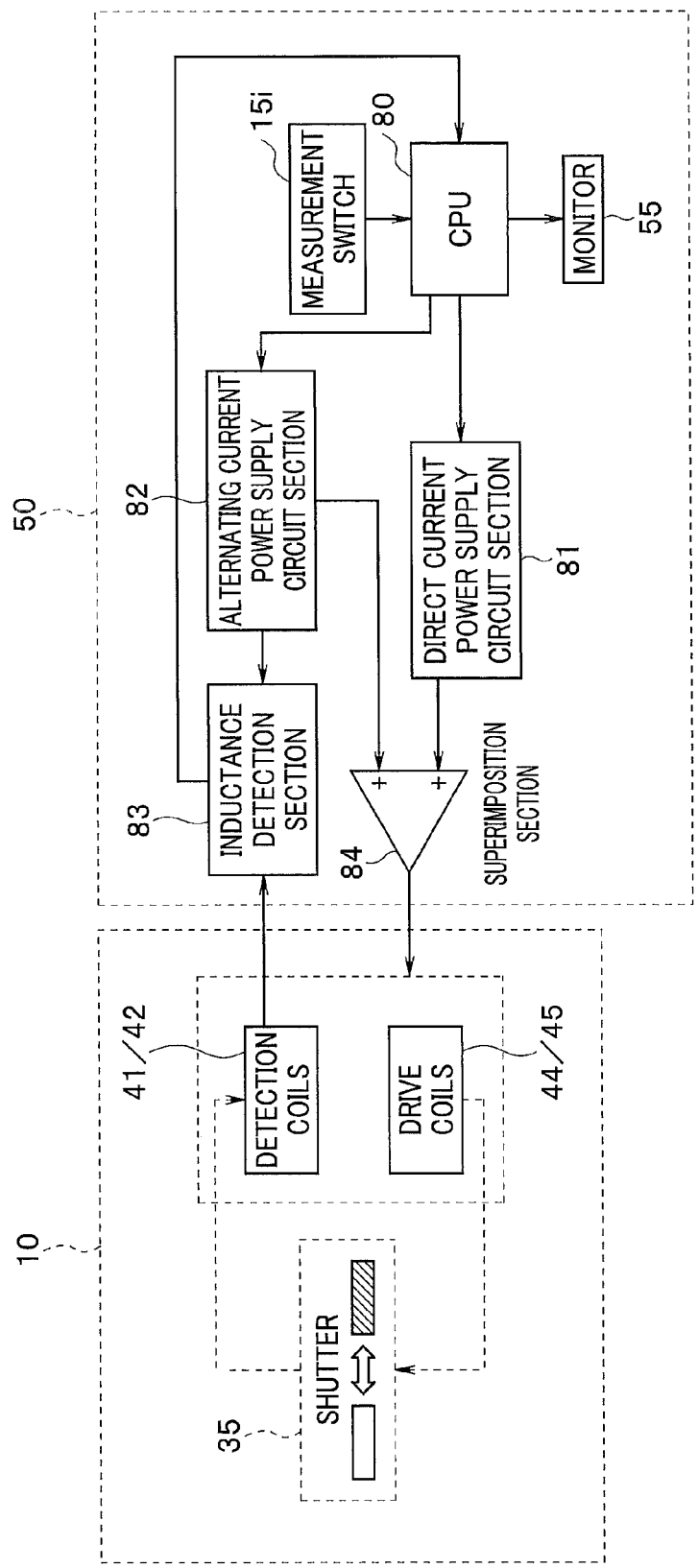
FIG. 8 is a block diagram schematically illustrating a circuit in the endoscope apparatus in FIG. 1, the circuit moving the light-blocking shutter and detecting the movement, in a modification in which the drive coils and the detection coils FIG. 6 are connected in series.

Another modification will be indicated with reference to FIG. 8. FIG. 8 is a block diagram schematically illustrating a circuit in the endoscope apparatus in FIG. 1, the circuit moving the light-blocking shutter and detecting the movement, in a modification in which the drive coils and the detection coils of FIG. 6 are connected in series.

The present embodiment described above indicates that the direct current power supply circuit section 81 is electrically connected to the drive coils 44 and 45; and direct current is provided to the drive coils 44 and 45 from the direct current power supply circuit section 81 by the drive control performed by the CPU 80.

Also, the present embodiment indicates that: the alternating current power supply circuit section 82 is electrically connected to the detection coils 41 and 42; and alternating current is provided to the detection coils 41 and 42 from the alternating current power supply circuit section 82 by the drive control performed by the CPU 80.

In other words, the present embodiment indicates that a circuit that provides direct current to the drive coils 44 and 45 and a circuit that provides alternating current to the detection coils 41 and 42 are provided separately.

The present invention is not limited to this case, and as illustrated in FIG. 8, it is possible that: drive coils 44 and 45 and detection coils 41 and 42 are connected in series; and the CPU 80 performs control to superimpose direct current from the direct current power supply circuit section 81 and alternating current from the alternating current power supply circuit section 82 on each other in a superimposition section 84 to provide the direct current and the alternating current superimposed on each other to the drive coils 44 and 45 and the detection coils 41 and 42. Note that, control performed by the CPU 80 to pivot the light-blocking shutter 35 and control performed by the CPU 80 to detect movement of the light-blocking shutter 35 are the same as those of the present embodiment described above except of the provision of direct current and alternating current superimposed on each other.

Even such configuration enables, in addition to provision of effects that are similar to those of the present embodiment described above, reduction in number of wirings to provide direct current and alternating current from four to two because of the serial connection between the drive coils 44 and 45 and the detection coils 41 and 42 and thus enabling effective use of a limited space inside the distal end portion 11.

Second Embodiment

Figure 9:
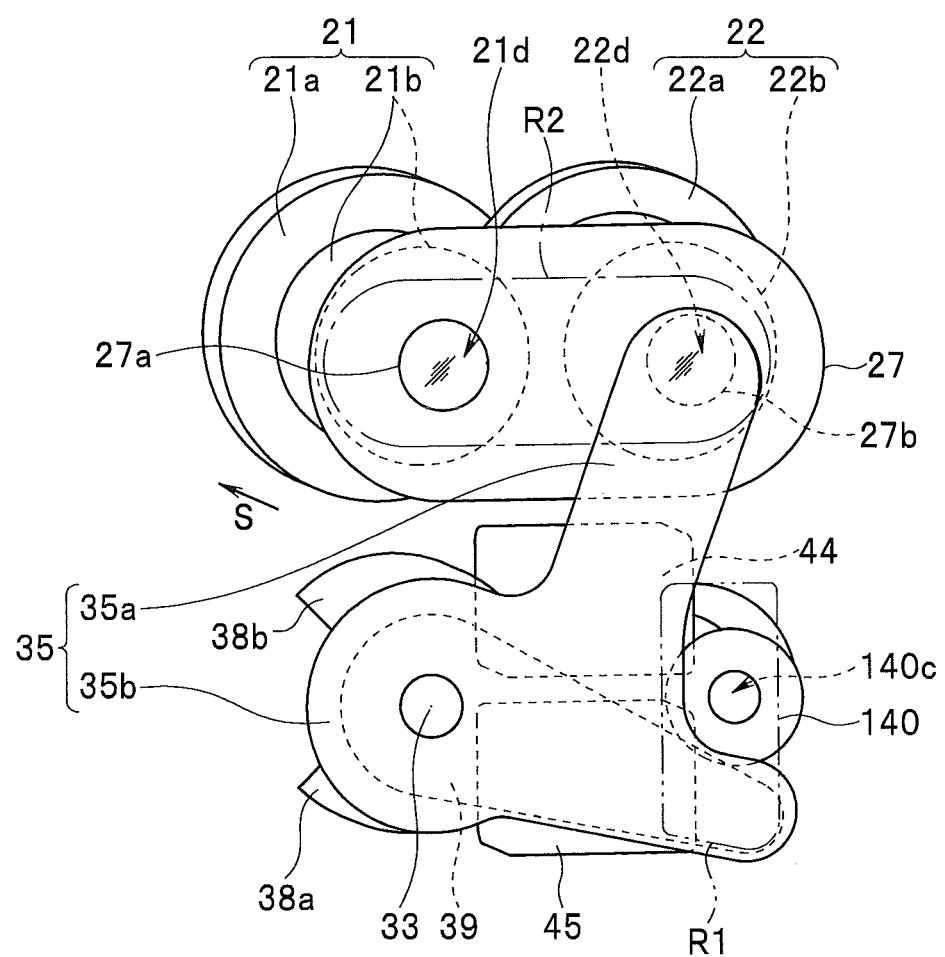
FIG. 9 is a perspective view illustrating an actuator unit in an image pickup unit provided in a distal end portion of an insertion portion of an endoscope in an endoscope apparatus according to a second embodiment, together with a first optical system, a second optical system and a diaphragm plate.
Figure 10:
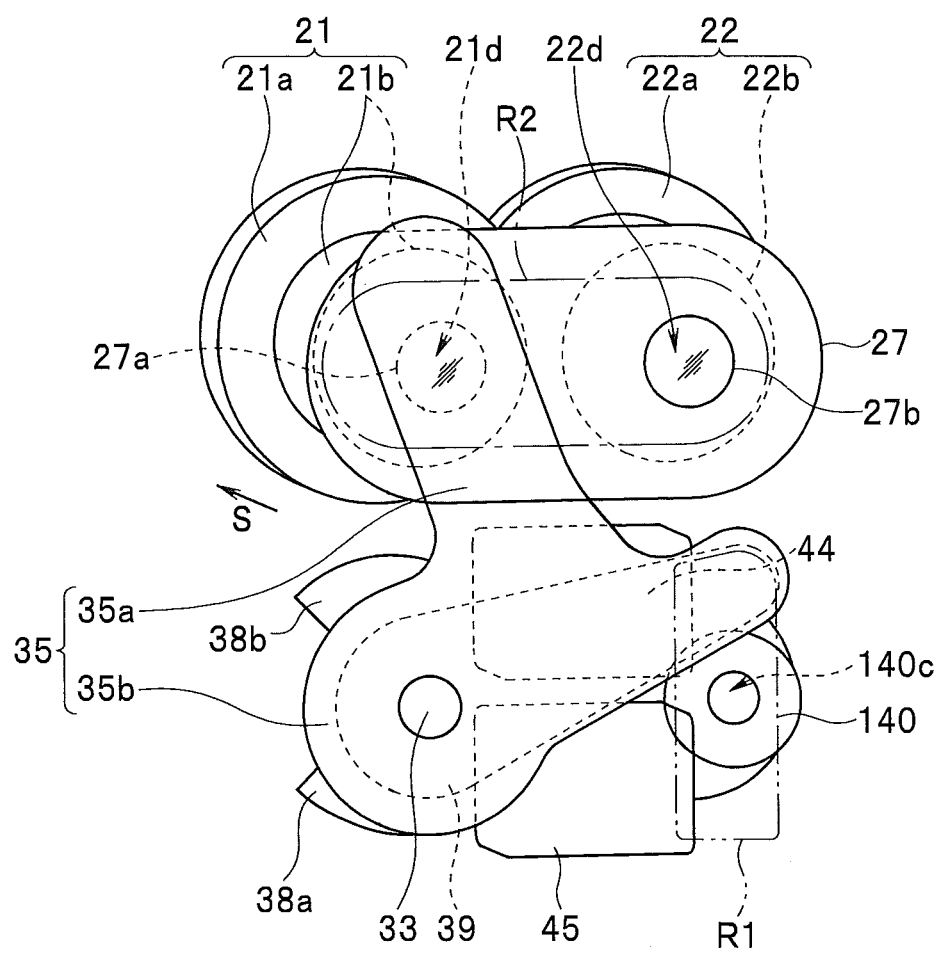
FIG. 10 is a perspective view illustrating the actuator unit in which a first optical path of the first optical system in FIG. 9 is blocked by a light-blocking shutter, together with the first optical system, the second optical system and the diaphragm plate.

FIG. 9 is a perspective view illustrating an actuator unit in an image pickup unit provided inside a distal end portion of an insertion portion of an endoscope in an endoscope apparatus according to the present embodiment, together with a first optical system, a second optical system and a diaphragm plate, and FIG. 10 is a perspective view illustrating an actuator unit in which a first optical path of the first optical system in FIG. 9 is blocked by a light-blocking shutter, together with the first optical system, the second optical system and the diaphragm plate.

Figure 11:
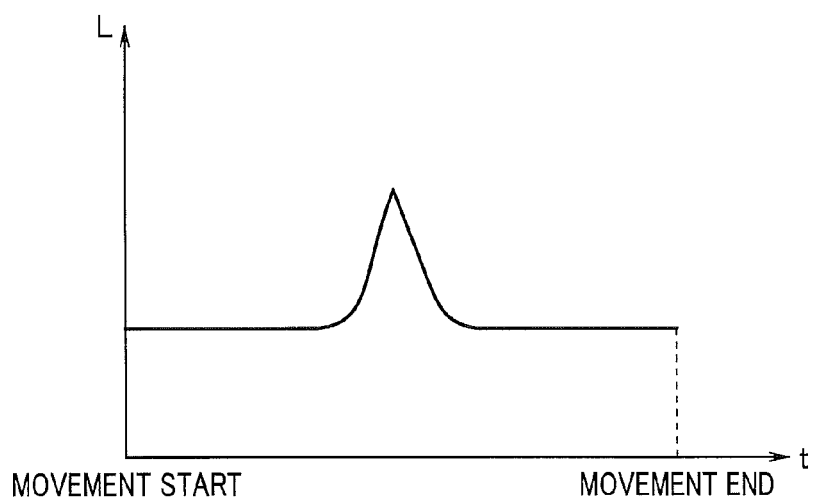
FIG. 11 is a graphic chart indicating inductance variation detected by an inductance detection section when a magnetic body blocked a hollow portion of the detection coil in FIGS. 9 and 10 for a fixed time period along with movement of the light-blocking shutter between a first position and a second position.

FIG. 11 is a graphic chart indicating inductance variation detected by an inductance detection section when a magnetic body blocked a hollow portion of the detection coil in FIGS. 9 and 10 for a fixed time period along with movement of the light-blocking shutter between the first position and the second position.

A configuration of the endoscope apparatus according to the second embodiment is different from that of the above-described endoscope apparatus according to the first embodiment illustrated in FIGS. 1 to 7 in that only one detection coil is included. Therefore, only this difference will be described, components that are similar to those of the first embodiment are provided with reference numerals that are the same as those of the first embodiment and description of such components will be omitted.

As illustrated in FIGS. 9 and 10, in the present embodiment, a major part of an actuator unit 30 includes a holding member 31, a magnet rotor 32, a pivot shaft 33, a light-blocking shutter 35, a yoke 38, drive coils 44 and 45 and a detection coil 140.

In the present embodiment, also, the light-blocking shutter 35 is pivotable between the first position illustrated in FIG. 10 in which a light-blocking portion 35*a* blocks a first optical path 21*d* of a first optical system 21 and the second position illustrated in FIG. 9 in which the light-blocking portion 35*a* blocks a second optical path 22*d* of a second optical system 22. A configuration in which the light-blocking shutter 35 is moved between the first position and the second position using the drive coils 44 and 45 is the same as that of the above-described first embodiment.

In the present embodiment, also, a magnetic body 39 is provided on a surface of a fixed portion 35*b* of the light-blocking shutter 35, the surface facing the detection coil 140.

Furthermore, in the present embodiment, as illustrated in FIGS. 9 and 10, the magnetic body 39 is formed so as to have a size and a shape that allow the magnetic body 39 to block a hollow portion 140*c* of the detection coil 140 at a position between the first position and the second position when the light-blocking shutter 35 is moved to a position between the first position and the second position, and release the hollow portion 140*c* when the light-blocking shutter 35 is moved to the first position or the second position.

Note that in the present embodiment, as described later, the detection coil 140 includes only one detection coil, and thus, the magnetic body 39 may be formed so as to have a size that allows the magnetic body 39 to cover the entire surface of the light-blocking shutter 35. Furthermore, the light-blocking shutter 35 itself may include the magnetic body 39.

Also, as illustrated in FIGS. 9 and 10, in the present embodiment, the detection coil 140 includes one detection coil, and at least the hollow portion 140c of the detection coil 140 is positioned in a pivoting region R1 of pivoting of the magnetic body 39 along with pivoting of the light-blocking shutter 35. More specifically, the detection coil 140 is fixed in abutment with a position between the drive coil 44 and the drive coil 45 on upper surfaces of the drive coils 44 and 45.

Also, in the present embodiment, although not illustrated, the detection coil 140 is provided relative to the drive coils 44 and 45 in such a manner that a magnetic field direction J1 inside the hollow portion 140c of the detection coil 140 and a magnetic field direction J2 inside each of hollow portions 44c and 45c of the drive coils 44 and 45 are perpendicular to each other.

As illustrated in FIGS. 9 and 10, the detection coil 140 is provided at a position between the first position and the second position of the light-blocking shutter 35.

Therefore, the light-blocking portion 35a of the light-blocking shutter 35 is formed so as to have a shape and a size that allow the light-blocking portion 35a to block neither the first optical path 21d nor the second optical path 22d when the magnetic body 39 blocks the hollow portion 140c. In other words, the light-blocking portion 35a is formed so as to have a shape and a size that allows the light-blocking portion 35a to block either the first optical path 21d or the second optical path 22d when the magnetic body 39 does not block the hollow portion 140c.

The detection coil 140 is used for detecting movement of the light-blocking shutter 35 by alternating current being provided to the detection coil 140 from an alternating current power supply circuit section 82 according to drive control performed by a CPU 80 to detect whether or not the magnetic body 39 blocks the hollow portion 140c.

In the present embodiment, the alternating current power supply circuit section 82 provides alternating current to the detection coil 140 according to the drive control performed by the CPU 80.

In the present embodiment, also, the alternating current power supply circuit section 82 may be configured to consistently provide alternating current to the detection coil 140 when power of the endoscope apparatus 100 is on or may be configured to provide alternating current only when a pivotal position of the light-blocking shutter 35 is detected.

Also, in the present embodiment, an inductance detection section 83 is intended to detect variation of an inductance L when the magnetic body 39 blocks the hollow portion 140c of the detection coil 140 according to the drive control performed by the CPU 80.

In the present embodiment, the CPU 80 performs control to provide alternating current to the detection coil 140 via the alternating current power supply circuit section 82 to detect variation of the inductance L when a magnetic field generated in the hollow portion 140c is blocked by the magnetic body 39, from a value of the alternating current via the inductance detection section 83 and thereby detect pivotal movement of the light-blocking shutter 35.

More specifically, as illustrated in FIG. 11, the CPU 80 detects that the light-blocking shutter 35 is moved from the first position to the second position or is moved from the second position to the first position when the CPU 80 detects temporal increase in the inductance L for a fixed time period t as a result of the magnetic body 39 temporarily blocking the magnetic field in the hollow portion 140c along with movement of the light-blocking shutter 35 between the first position and the second position.

Furthermore, if the CPU 80 cannot detect variation of the inductance L even though direct current is provided to the drive coils 44 and 45 during alternating current being provided to each detection coil 140, the CPU 80 detects that the light-blocking shutter 35 is in a non-moving state and performs control to provide a warning via, for example, a monitor 55, the warning indicating that measurement values of an observed site obtained via an image pickup device 24 are incorrect. Note that the warning is not limited to display and may be, for example, sound.

Note that the other components are the same as those of the above-described first embodiment.

Next, operation of the present embodiment will be described. The description will be provided only on differences from the first embodiment.

First, when the light-blocking shutter 35 is moved from the first position to the second position or from the second position to the first position as a result of direct current being provided to the drive coils 44 and 45, the magnetic body 39 temporarily blocks the hollow portion 140c of the detection coil 140 while the magnetic body 39 moving, along with the movement of the light-blocking shutter 35.

Here, the CPU 80 detects temporal increase in value of the inductance L as illustrated in FIG. 11 for the fixed time period t as a result of the magnetic body 39 temporarily blocking the magnetic field in the hollow portion 140c, from variation in current value of the alternating current via the inductance detection section 83. Thus, the CPU 80 detects that the light-blocking shutter 35 is moved from the first position to the second position or is moved from the second position to the first position. Note that the CPU 80 may cause the monitor 55 to provide display indicating that the light-blocking shutter 35 is moved to the first position or the second position.

Note that, if there is no variation in the value of the inductance L, the CPU 80 detects that the light-blocking shutter 35 is not moved to the first position or the second position and causes the monitor 55 to display a warning.

In the configuration according to the present embodiment, only one detection coil is provided, and thus, it is possible to detect that the light-blocking shutter 35 is moved from the first position to the second position or is moved from the second position to the first position, but, as opposed to the above-described first embodiment, it is impossible to detect a direction of pivoting of the light-blocking shutter 35, that is, whether the light-blocking shutter 35 is moved to the first position or is moved to the second position, via the detection coil 140.

However, it is possible to detect whether the light-blocking shutter 35 is moved to the first position or is moved to the second position, from a direction of the direct current provided to the drive coils 44 and 45. Note that the other operations are the same as those of the above-described first embodiment.

Such configuration as above requires only one detection coil, and thus, enables in addition to simplification of the configuration of the actuator unit 30, further reduction in diameter and length of the distal end portion 11 compared to the first embodiment. Note that the other effects are the same as those of the above-described first embodiment.

Figure 12:
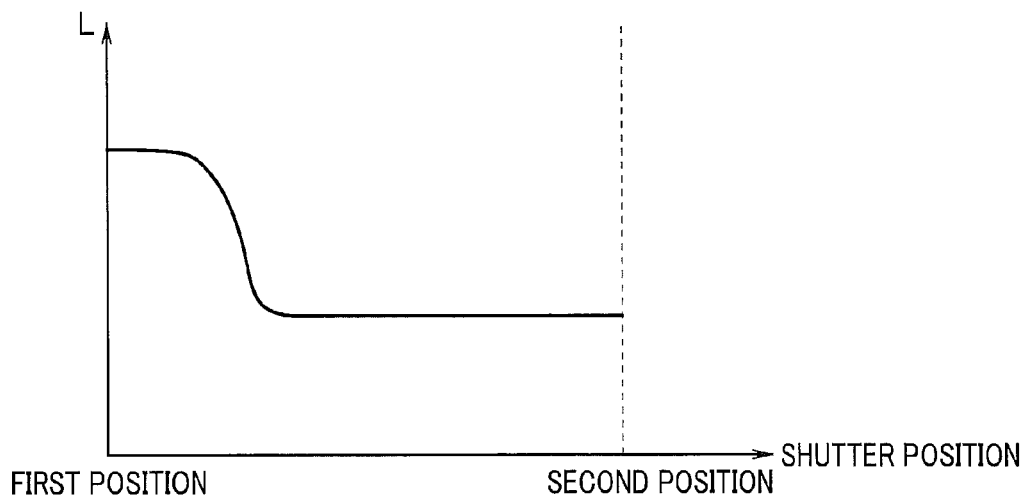
FIG. 12 is a graphic chart indicating inductance variation detected by the inductance detection section when the detection coil in FIGS. 9 and 10 is provided at the first position or the second position, between the first position and the second position of the light-blocking shutter.

Note that a modification will be indicated below with reference to FIG. 12. FIG. 12 is a graphic chart indicating inductance variation detected by the inductance detection section when the detection coil in FIGS. 9 and 10 is provided at the first position or the second position, between the first position and the second position of the light-blocking shutter.

The present embodiment described above indicates that the detection coil 140 is provided at a position between the first position and the second position in the pivoting region R1 of the magnetic body 39.

The present invention is not limited to this case, and the detection coil 140 may be provided at the first position or the second position in the pivoting region R1.

In this case, the magnetic body 39 is formed so as to have a size and a shape that allows the magnetic body 39 to block the hollow portion 140*c* of the detection coil 140 when the light-blocking shutter 35 is moved to the first position, and release the hollow portion 140*c* when the light-blocking shutter 35 is moved to the second position.

In such configuration, for example, if the detection coil 140 is provided at the first position, the CPU 80 can detect substantial increase in the inductance L as illustrated in FIG. 12 when the magnetic body 39 blocks the hollow portion 140*c* of the detection coil 140 at the first position along with movement of the light-blocking shutter 35 from the second position to the first position, and thus can steadily detect that the light-blocking shutter 35 is moved from the second position to the first position.

Also, the CPU 80 can detect substantial decrease in the inductance L as illustrated in FIG. 12 when the magnetic body 39 releases the hollow portion 140*c* of the detection coil 140 at the second position along with movement of the light-blocking shutter 35 from the first position to the second position, and thus, can steadily detect that the light-blocking shutter 35 is moved from the first position to the second position. Note that the above applies to the case where the detection coil 140 is provided at the second position. The other effects are similar to those of the present embodiment described above.

Third Embodiment

Figure 13:
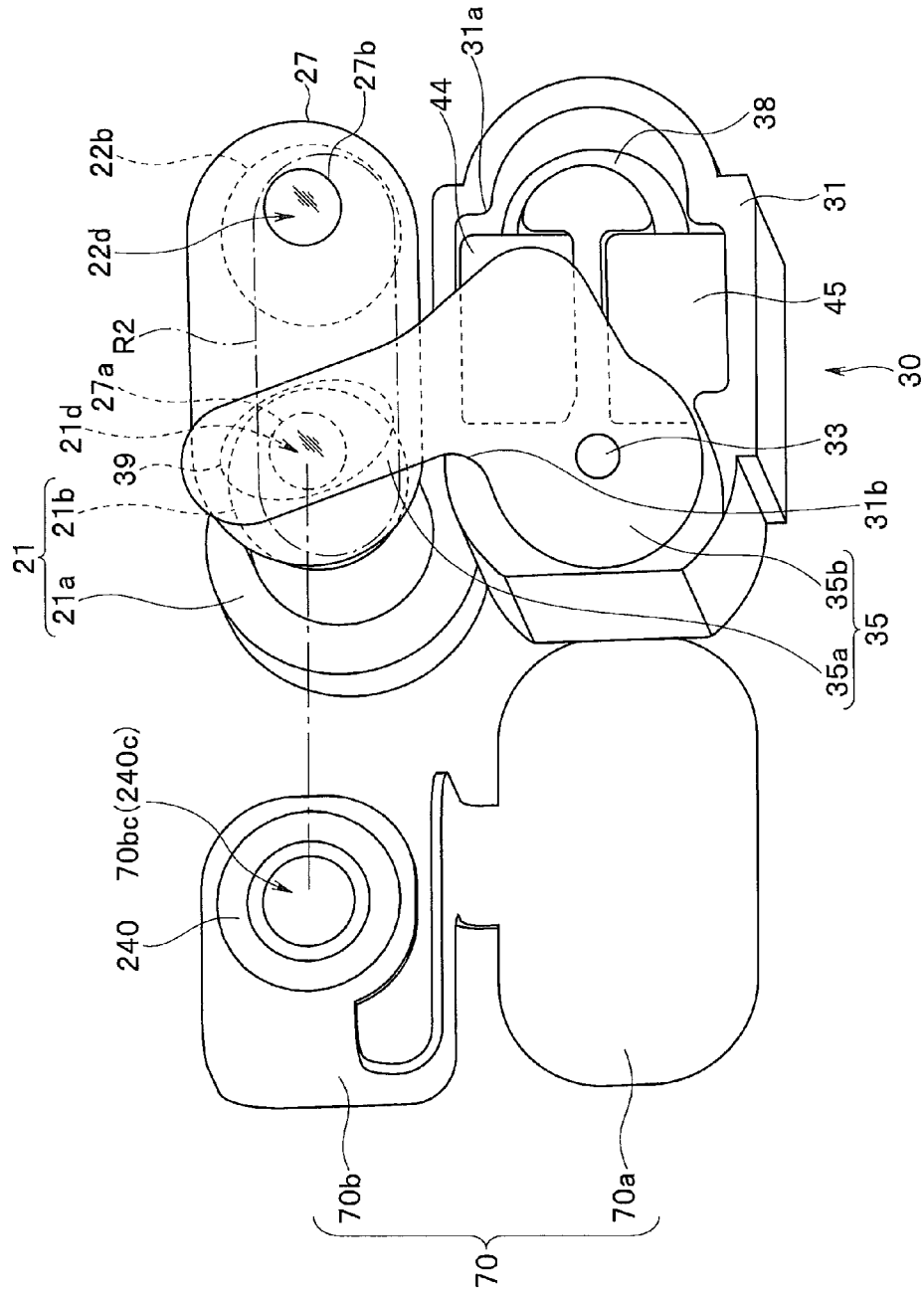
FIG. 13 is a perspective view illustrating a configuration in an endoscope apparatus according to a third embodiment in which a detection coil is provided on a flexible substrate that is attachable/detachable to/from an actuator unit in an image pickup unit provided inside a distal end portion of an insertion portion of an endoscope.

FIG. 13 is a perspective view illustrating a configuration in an endoscope apparatus according to the present embodiment in which a detection coil is provided on a flexible substrate that is attachable/detachable to/from an actuator unit in an image pickup unit provided inside a distal end portion of an insertion portion of an endoscope.

A configuration of the endoscope apparatus according to the third embodiment is different from the above-described endoscope apparatus according to the first embodiment illustrated in FIGS. 1 to 7 and the endoscope apparatus according to the second embodiment illustrated in FIGS. 9 to 11 in that a detection coil is provided on a flexible substrate. Therefore, description will be provided only on this difference, components that are similar to those of the first and second embodiments are provided with reference numerals that are the same as those of the first and second embodiments and description of the components will be omitted.

As in the second embodiment, the present embodiment will be described taking a case where only one detection coil is used, as an example.

As illustrated in FIG. 13, in the present embodiment, a flexible substrate 70 is attachable/detachable to/from an actuator unit 30.

A major part of the flexible substrate 70 includes a first part 70*a* to be attached to a proximal end face of a holding member 31, and a second part 70*b* to be attached to a part of a proximal end face of a diaphragm plate 27, the part overlapping with a first optical system 21.

At a position in the second part 70*b* where the second part 70*b* overlaps with a diaphragm aperture 27*a* of the diaphragm plate 27, an opening 70*bc* having a size that is substantially the same as that of the diaphragm aperture 27*a* is formed. The opening 70*bc* allows a first light flux to enter a rear lens group 23.

At a position in a proximal end face of the second part 70*b*, the position surrounding the opening 70*bc*, a detection coil 240 formed as a coil pattern is provided. Thus, the opening 70*bc* forms a hollow portion 240*c* of the detection coil 240.

Note that in the present embodiment, also, a light-blocking shutter 35 is pivotable between a first position in which a light-blocking portion 35*a* blocks a first optical path 21*d* of the first optical system 21 and a second position in which the light-blocking portion 35*a* blocks a second optical path 22*d* of a second optical system 22. Note that the configuration in which the light-blocking shutter 35 is moved between the first position and the second position using drive coils 44 and 45 is the same as those of the above-described first and second embodiments.

In the present embodiment, also, a magnetic body 39 is provided on a surface of the light-blocking portion 35*a* of the light-blocking shutter 35, the surface facing the detection coil 240.

The magnetic body 39 is formed so as to have a size and a shape that allow the magnetic body 39 to block the hollow portion 240*c* of the detection coil 240 when the light-blocking shutter 35 is moved to the first position, and release the hollow portion 240*c* when the light-blocking shutter 35 is moved to the second position.

Note that, as in the second embodiment, in the present embodiment, also, the magnetic body 39 may be formed so as to have a size that allows the magnetic body 39 to cover the entire surface of the light-blocking shutter 35. Furthermore, the light-blocking shutter 35 itself may include the magnetic body 39.

Also, in the present embodiment, as the detection coil 240, only one detection coil is included, and the detection coil 240 is provided at the first position where, after the second part 70*b* of the flexible substrate 70 is attached to the diaphragm plate 27, the light-blocking shutter 35 occludes the first optical path 21*d* and the magnetic body 39 occludes the hollow portion 240*c*. In other words, at least the hollow portion 240*c* of the detection coil 240 is provided at the first position of the light-blocking shutter 35 within a region R2 connecting the first optical path 21*d* and the second optical path 22*d*.

Furthermore, in the present embodiment, also, although not illustrated, the detection coil 240 is provided relative to the drive coils 44 and 45 in such a manner that a magnetic field direction J1 in the hollow portion 240*c* of the detection coil 240 and a magnetic field direction J2 in each of hollow portions 44*c* and 45*c* of the drive coils 44 and 45 are perpendicular to each other.

In such configuration, as in the above-described modification of the second embodiment, the CPU 80 can detect substantial increase in an inductance L as illustrated in FIG. 12 when the magnetic body 39 blocks the hollow portion 240*c* of the detection coil 240 at the first position along with movement of the light-blocking shutter 35 from the second position to the first position, and thus can steadily detect that the light-blocking shutter 35 is moved from the second position to the first position.

Also, the CPU 80 can detect substantial decrease in the inductance L as illustrated in FIG. 12 when the magnetic body 39 releases the hollow portion 240*c* of the detection coil 240 at the second position along with movement of the light-blocking shutter 35 from the first position to the second position, and thus can steadily detect that the light-blocking shutter 35 is moved from the first position to the second position. Note that the above applies to the case where the detection coil 240 is provided at the second position using the flexible substrate 70.

Note that the other components and operations are the same as those of the above-described second embodiment.

Operation and effects that are similar to those of the second embodiment may be provided by providing the detection coil 240 between the first position and the second position in the region R2, using the flexible substrate 70.

Furthermore, operation and effects that are similar to those of the first embodiment may be provided by providing two detection coils on the proximal end face of the second part 70*b* of the flexible substrate 70 and locating the detection coils at the first position and the second position, respectively, in the region R2 when the second part 70*b* is attached to the proximal end face of the diaphragm plate 27.

Such configuration enables the detection coil to be provided separately from the actuator unit 30, that is, separately from the holding member 31, and thus enables reduction in size of the holding member 31, and thus enables, in addition to further reduction in diameter and length of the distal end portion 11 compared to those of the first and second embodiments, enhancement in workability and assemblability because of simplification of wirings to the detection coil. Note that the detection coil may be provided inside the holding member 31 using the flexible substrate 70 if size reduction is ignored. Note that the other effects are the same as those of the above-described first and second embodiments.

Note that a modification will be indicated below. Although the above-described first and second embodiments indicate that the detection coils 41 and 42 or the detection coil 140 is provided within the region R1 in abutment with the upper faces of the drive coils 44 and 45, the present invention is not limited to this case, and as indicated in the third embodiment, it should be understood that detection coil(s) may be fixed to the diaphragm plate 27 within the region R2 in the proximal end face of the diaphragm plate 27.

Also, although the above-described first to third embodiments indicate that the CPU 80 performs measurement of an observed site from two still images, which are a first image and a second image picked up by the image pickup device 24, the present invention is not limited to this case, and it should be understood that it is possible to pick up a three-dimensional movie from a plurality of first images and a plurality of second images by repeatedly picking up a first image and a second image with a time difference provided by moving the light-blocking shutter 35 and perform measurement of an observed site from the video image.

Note that in such configuration, the CPU 80 may be configured to, in detection of movement of the light-blocking shutter 35, only if no variation in the inductance L is detected, for example, three consecutive times after provision of direct current to the drive coils 44 and 45, cause the monitor 55 to display a warning.

Furthermore, although each of the above first to third embodiments has been described taking an industrial endoscope apparatus as an example, it should be understood that the present invention may be applied to medical endoscope apparatuses.

What is claimed is:

1. An endoscope apparatus comprising:
a first optical system for observing an inside of an object, the first optical system being provided in an insertion portion of an endoscope to be inserted to the object;
a second optical system for observing the inside of the object, the second optical system being provided in the insertion portion and providing parallax relative to the first optical system;
a light-blocking shutter that is pivotable between a first position in which the light-blocking shutter blocks a first optical path of the first optical system and a second position in which the light-blocking shutter blocks a second optical path of the second optical system, a magnetic body being formed on at least a part of the light-blocking shutter or at least a part of the light-blocking shutter includes a magnetic body;
a magnet rotor fixed to a pivot shaft of the light-blocking shutter;
a drive coil that upon direct current being provided to the drive coil, provides a magnetic force to the magnet rotor to pivot the light-blocking shutter from the first position to the second position or from the second position to the first position;
a detection coil provided in a pivoting region of pivoting of the magnetic body along with pivoting of the light-blocking shutter, alternating current being provided to the detection coil;
an image pickup device that individually forms a first image of an observed site of the object observed via the first optical system and a second image of the observed site observed via the second optical system, the second image exhibiting parallax relative to the first image, on an entire light-receiving surface with a time difference provided by the light-blocking shutter; and
a control section provided inside the endoscope or an apparatus body to which the endoscope is connected, the control section performing measurement of the observed site from the first image and the second image formed on the light-receiving surface of the image pickup device,
wherein the control section performs control to provide the direct current to the drive coil and performs control to provide the alternating current to the detection coil, and where the alternating current is provided to the detection coil, the control section detects a pivotal position of the light-blocking shutter by detecting variation of an inductance when a magnetic field generated in a hollow portion of the detection coil is blocked by the magnetic body, from a value of the alternating current.

2. The endoscope apparatus according to claim 1, wherein if the control section cannot detect variation of the inductance even though the direct current is provided to the drive coil during the alternating current being provided to the detection coil, the control section detects that the light-blocking shutter is in a non-moving state, and performs control to provide a warning indicating that a measurement value of the observed site obtained via the image pickup device is incorrect.

3. The endoscope apparatus according to claim 1, further comprising a direct current power supply that provides the direct current to the drive coil according to drive control performed by the control section, and an alternating current power supply that provides the alternating current to the detection coil according to the drive control performed by the control section, wherein:
the direct current power supply, the alternating current power supply, the drive coil and the detection coil are connected in series; and the control section performs control to provide the direct current and the alternating current superimposed on each other to the drive coil and the detection coil.

4. The endoscope apparatus according to claim 1, wherein the detection coil is provided relative to the drive coil in such a manner that a direction of the magnetic field generated by the hollow portion of the detection coil and a direction of a magnetic field generated by a hollow portion of the drive coil are perpendicular to each other.

5. The endoscope apparatus according to claim 1, wherein the detection coil includes two detection coils, the hollow portion of one of the detection coils being blocked by the magnetic body in the first position, and the hollow portion of another of the detection coils being blocked by the magnetic body in the second position.

6. The endoscope apparatus according to claim 5, wherein:
one of the detection coils has a larger number of coil element wire turns than a number of coil element wire turns of another of the detection coils;
the control section detects that the light-blocking shutter is moved from the first position to the second position or is moved from the second position to the first position, by detecting a difference in the inductance generated as a result of the magnetic body blocking the magnetic fields in the hollow portions of the respective detection coils along with pivoting of the light-blocking shutter in the first position and the second position, the difference being attributable to the difference in number of turns, and
the control section detects that the light-blocking shutter is located between the first position and the second position, by detecting decrease in the inductance generated by the magnetic body releasing the magnetic field in the hollow portion of each of the detection coils along with pivoting of the light-blocking shutter.

7. The endoscope apparatus according to claim 5, wherein the magnetic body is formed so as to have a size that allows the magnetic body to block the magnetic field in the hollow portion of the one of the detection coils and release the magnetic field in the hollow portion of the other of the detection coils when the light-blocking shutter is moved to the first position and block the magnetic field in the hollow portion of the other of the detection coils and release the magnetic field in the hollow portion of the one of the detection coils when the light-blocking shutter is moved to the second position.

8. The endoscope apparatus according to claim 1, wherein the detection coil includes one detection coil.

9. The endoscope apparatus according to claim 8, wherein:
the detection coil is provided at a position between the first position and the second position; and
when the control section detects temporary increase in the inductance for a fixed time period as a result of the magnetic body temporarily blocking the magnetic field in the hollow portion along with pivoting of the light-blocking shutter, the control section detects that the light-blocking shutter is moved from the first position to the second position or is moved from the second position to the first position.

10. The endoscope apparatus according to claim 8, wherein:
the detection coil is provided at the first position or the second position; and
when the control section detects increase or decrease in the inductance as a result of the magnetic body blocking or releasing the magnetic field in the hollow portion at the first position or the second position along with pivoting of the light-blocking shutter, the control section detects that the light-blocking shutter is moved from the first position to the second position or is moved from the second position to the first position.

11. The endoscope apparatus according to claim 8, wherein the magnetic body is formed so as to have a size that allows the magnetic body to cover an entire surface of the light-blocking shutter.

12. The endoscope apparatus according to claim 1, wherein the detection coil is provided in abutment with the drive coil.

13. The endoscope apparatus according to claim 1, wherein the detection coil is provided within a region connecting the first optical path and the second optical path.

14. The endoscope apparatus according to claim 1, wherein the detection coil is formed in a coil pattern on a flexible substrate.

* * * * *